(12) United States Patent
Arakawa et al.

(10) Patent No.: US 8,168,406 B2
(45) Date of Patent: May 1, 2012

(54) DRY ANALYTICAL ELEMENT FOR LIPASE MEASUREMENT

(75) Inventors: Jun Arakawa, Kanagawa (JP); Nobuhito Masuda, Asaka (JP); Kentaro Nakamura, Asaka (JP); Shigeki Kageyama, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 530 days.

(21) Appl. No.: 12/410,035

(22) Filed: Mar. 24, 2009

(65) Prior Publication Data

US 2009/0246811 A1   Oct. 1, 2009

(30) Foreign Application Priority Data

Mar. 25, 2008 (JP) ................................. 2008-077542

(51) Int. Cl.
*C12Q 1/44* (2006.01)
*C12M 1/36* (2006.01)
*C12M 1/34* (2006.01)
*C12M 1/00* (2006.01)

(52) U.S. Cl. .................... 435/19; 435/287.5; 435/287.7; 435/287.9

(58) Field of Classification Search .................... 435/19, 435/287.3, 287.5, 287.7
See application file for complete search history.

(56) References Cited

U.S. PATENT DOCUMENTS 4,555,483 A    11/1985   LiMuti et al.

FOREIGN PATENT DOCUMENTS

| FR | 2 619 219 A1 | 2/1989 |
|---|---|---|
| JP | 59-48098 A | 3/1984 |
| JP | 4-316500 A | 11/1992 |
| JP | 9-154598 A | 6/1997 |
| JP | 2002-125699 A | 5/2002 |

OTHER PUBLICATIONS

Tetrault, "Lipase Activity in Serum Measured with Ektachem is Often Increased in Nonpancreatic Disorders", Clinical Chemistry, vol. 37, No. 3, 1991, pp. 447-451.

*Primary Examiner* — Herbert J Lilling
(74) *Attorney, Agent, or Firm* — Birch, Stewart, Kolasch & Birch, LLP

(57) ABSTRACT

The present invention provides a method for producing a dry analytical element for measurement of pancreatic lipase contained in a body fluid which contains triglyceride of long chain alkyl fatty acid having 12 to 22 carbon atoms, monoglyceride lipase, and a glycerine measurement reagent, and comprises a water-impermeable support and at least one spreading or reagent layer, said method comprising the step of coating an emulsion/dispersion solution of triglyceride with an average particle size of 1 μm or less.

17 Claims, No Drawings

DRY ANALYTICAL ELEMENT FOR LIPASE MEASUREMENT

TECHNICAL FIELD

The present invention relates to: a dry analytical element for measurement of lipase activity, and particularly pancreatic lipase activity, in a liquid sample such as, in particular, the serum or plasma of humans and animals, such analytical element being available for convenient use and having high accuracy; and a method for producing the same. The dry analytical element of the present invention is particularly useful for diagnosing human and canine pancreatic diseases.

BACKGROUND ART

Pancreatic lipase analysis, which is useful for pancreatic disease diagnosis, is often carried out by measuring pancreatic lipase under conditions in which a micellar substrate is dispersed in water in view of the fact that pancreatic lipase functions in oil-water interface. This is because non-pancreatic lipase such as lipoprotein lipase or esterase reacts with a substrate solubilized with a surfactant or the like or with glyceride comprising fatty acid having short alkyl chains. Thus, it is considered that a technically important point for development of dry analytical elements for pancreatic lipase is the incorporation of a long-fatty-acid glyceride serving as a substrate, which is specific to pancreatic lipase, into such analytical element, provided that glyceride is in a state such that it is specific to pancreatic lipase.

Dry analytical elements used for lipase analysis are roughly classified into two types. An example of a first type is a dry analytical element obtained by a method using 1,2-O-dilauryl-rac-glycero-3-glytaric acid/resorufin ester serving as a dye-releasing substrate (JP Patent Publication (Kokai) No. 9-154598 A (1997)). Such method is preferable because high specificity with respect to pancreatic lipase can be achieved and a glycerin coloring system is unnecessary. However, such substrate incorporated into a dry analytical element is highly likely to disintegrate. Thus, such dry analytical element has still not been available in practice, although it has been attempted to separate a low-pH layer containing a lipase substrate from another high-pH reagent layer. In addition, the relatively high price of such a substrate is also problematic in terms of practical use.

An example of a second type is a dry analytical element for lipase analysis, in which a method for converting triglyceride used as a substrate into a dye via glycerin and hydrogen peroxide is used. According to the first disclosed method, it is a multilayer dry analytical element (JP Patent Publication (Kokai) No. 59-48098 A (1984)), wherein triglyceride having a long chain alkyl group having at least 8 carbon atoms at an ester position (α position) and two other esters each having a short chain alkyl group is used as a substrate, water-soluble 1,2 diacetylglyceride generated in the presence of lipase in a specimen is converted into glycerin with the use of an esterase (namely, acetinase), and glycerin is converted into a dye. The above method is a convenient and highly accurate lipase measurement method. However, it has been reported that selectivity with respect to pancreatic lipase is not high, and thus that attention is required if this method is applied to the diagnosis of pancreatic diseases [Clin. Chem., 37/3, 447-451 (1991)]. Such problem regarding specificity may be caused by the fact that triglyceride used as a substrate also contains a short chain alkyl group.

Next, there has been disclosed a method, which also uses triglyceride as a substrate. That is, there has been disclosed a dry chemistry reagent for pancreatic lipase analysis, which comprises triglyceride having only a long chain fatty acid containing 14 to 20 carbon atoms, such as triolein, as a substrate and which further comprises monoglyceride lipase and a glycerin measurement reagent (JP Patent Publication (Kokai) No. 4-316500 A (1992)). Such a method using triolein is anticipated to be highly specific to pancreatic lipase. However, in this triolein addition method, since a highly fat-soluble substrate is incorporated, a protective colloid such as gum Arabic is used to carry out aqueous emulsification dispersion involving an ultrasonic treatment (JP Patent Publication (Kokai) No. 4-316500 A (1992): Examples). In this emulsification dispersion method, it is necessary to maintain the reproducibility of substrate dispersion and uniformity in particle size distribution. Thus, it is thought that production by such method is difficult.

For instance, JP Patent Publication (Kokai) No. 4-316500 A (1992) contains the following description: "triglyceride, such as triolein, comprising a long chain fatty acid in each of three ester positions has the property of being emulsified with difficulty. Thus, even if a solution in which triolein has been uniformly emulsified and dispersed via agitation or by physical shearing force generated by ultrasound waves or the like is added in the presence of a surfactant or a protective colloid upon preparation of a dry reagent, water serving as a dispersion medium disappears when the reagent becomes dry, and thus an emulsified product aggregates or coalesces so as to adhere to the surface of a spreading layer, resulting in significant reduction in the surface area in oil-water interface. Upon measurement, even if a specimen (liquid) containing lipase is allowed to react with such dry reagent, triolein remains in a state of aggregating or coalescing and thus does not return to the original state of being dispersed because of lack of physical shearing force. The reaction field of lipase is an oil-water interface. Thus, a decrease in the surface area of an oil-water interface is thought to cause a decrease in reaction rate."

In addition, in the examples of the method of JP Patent Publication (Kokai) No. 4-316500 A (1992), a filter and a nylon film is impregnated with a reagent. However, since a support is not used to maintain strength in the examples, it is considered difficult to carry out transportation and winding at a constant rate/high rate in the production process. Thus, in order to produce a dry analytical element having both measurement accuracy and productivity, addition of a support is almost essential.

A method modified from the method of JP Patent Publication (Kokai) No. 4-316500 A (1992), which comprises adding a support to produce a multilayer analytical element with high accuracy and incorporating fine particles therein so as to enhance lipase reactivity is described in JP Patent Publication (Kokai) No. 2002-125699 A. The applicant has further modified this method. The applicant has conceived of a method of adding glyceride, such as triolein, dissolved in an organic solvent such as ethanol to an analytical element comprising a support, thereby producing a dry analytical element that is highly specific to pancreatic lipase.

However, when such a dry analytical element comprising a support necessary for stable production and using triolein as a substrate was produced, unexpectedly, another serious problem occurred. That is to say, the following was found. That is, since triolein is oil, such triolein added to the reaction layer of lipase is easily transcribed on the back side of the support when the transported product is wound, and the transcribed triolein on the support is then transcribed on a pass roll used in transportation. The thus transcribed triolein reduces a friction between the pass roll necessary for transportation and the support, and transportation slip is thereby generated. In order to produce highly accurate dry analytical element, it is necessary to add a constant amount of reagent by coating, impregnation, etc. Generation of a slip during transportation makes addition of a constant amount of reagent impossible. This makes production of a dry analytical element for lipase measurement impossible. At the same time, it means that a producing apparatus having a transportation system, which has become contaminated by oil, cannot be used to produce products (e.g. a glucose analyzing device, a cholesterol analyzing device, etc.) used in highly accurate clinical analyses that require addition of a constant amount of reagent. Moreover, triolein transcribed on the support not only causes malfunction to the transportation system, but it also gives a positive error when it is transcribed on a device for measuring and analyzing neutral fats.

Due to the aforementioned problems, the product disclosed in JP Patent Publication (Kokai) No. 59-48098 A (1984) is still the only commercially available dry analytical element for lipase analysis, although the product has low pancreatic lipase specificity. Thus, dry analytical elements that are excellent in terms of reliability for diagnosis of pancreatic diseases have been awaited in the market.

DISCLOSURE OF THE INVENTION

It is an object of the present invention to provide: a dry analytical element for analyzing pancreatic lipase, which uses long chain fatty acid triglyceride such as triolein as a substrate and which comprises a support, wherein the triglyceride is not transcribed on the support to contaminate a transportation slip or other analytical elements and wherein an additive solution of the triglyceride neither reaggregates nor precipitate, so that the dry analytical element is stable and is compatible with production; and a method for producing the same.

In view of the above circumstances, the present inventors have conducted intensive studies. As a result, they have found that a multilayer dry analytical element can be stably produced under the following conditions. Triglyceride of long-chain fatty acid which is highly specific to pancreatic lipase is used. For a color development method, monoglyceride lipase and a glycerine coloring system are used. The structure of a dry multilayer analytical element is designed to contain a support that allows simple analysis with high precision. As a method of addition of triglyceride of long-chain fatty acid, an emulsion/dispersion solution of triglyceride with an average particle size of 1 μm or less is coated, which has never been used for a multilayer dry analytical element. Coating in such a manner results in a decrease in the amount of triglyceride transferred to a support, reduction or prevention of the occurrence of slipping upon delivery in the production step, and no contamination of a triglyceride to analytical slide. In addition, an emulsified product can be stabilized. This has led to the completion of the present invention.

The present invention provides a method for producing a dry analytical element for measurement of pancreatic lipase contained in a body fluid which contains triglyceride of long chain alkyl fatty acid having 12 to 22 carbon atoms, monoglyceride lipase, and a glycerine measurement reagent, and comprises a water-impermeable support and at least one spreading or reagent layer, said method comprising the step of coating an emulsion/dispersion solution of triglyceride with an average particle size of 1 μm or less.

Preferably, the average particle size of triglyceride is 0.5 μm or less.

Preferably, the average particle size of triglyceride is 0.3 μm or less.

Preferably, the emulsion/dispersion solution of triglyceride is prepared by high-pressure emulsification at a pressure of 100 MPa or more.

Preferably, the emulsion/dispersion solution of triglyceride contains a hydrophilic polymer.

Preferably, the emulsion/dispersion solution of triglyceride contains a hydrophilic polymer at 5 g/m$^2$ or more.

Preferably, the emulsion/dispersion solution of triglyceride contains a hydrophilic polymer at 10 g/m$^2$ or more.

Preferably, the hydrophilic polymer is a hydrophilic polymer selected from the group consisting of polyvinyl pyrrolidone, polyacrylamide, a cellulose derivative, gelatin, and combination thereof.

Preferably, the cellulose derivative is hydroxypropyl cellulose, hydroxyethyl cellulose, or methyl cellulose.

Preferably, the emulsion/dispersion solution of triglyceride contains at least hydroxypropyl cellulose or gelatin.

Preferably, triglyceride is triolein.

Preferably, monoglyceride lipase is derived from *Bacillus stearothermophilus* H-165.

Preferably, the glycerine measurement reagent contains glycerokinase, glycerophosphate oxidase, peroxidase, and a coloring reagent.

Preferably, the dry analytical element for measurement of pancreatic lipase contained in a body fluid comprises a water-impermeable support, a reagent layer, and a spreading layer.

Preferably, the spreading layer comprises a fabric or a porous membrane.

Preferably, the porous membrane is a porous membrane of polysulfone or acetyl cellulose or a porous membrane formed with fine beads.

The present invention further provides a dry analytical element for measurement of pancreatic lipase contained in a body fluid, which is produced by the aforementioned method according to the present invention.

A dry analytical element for measuring pancreatic lipase contained in body fluid was produced, which comprises triglyceride of long chain fatty acid having 12 to 22 carbon atoms, monoglyceride lipase, and a glycerin measurement reagent, and which comprises a water-impermeable support and at least one spreading or reagent layer. As a result, a dry analytical element having good basic performance could be produced, but upon transportation during the production process, the support was slipped, and thus it became impossible to conduct transportation at a constant rate. This is because a friction of the support was reduced due to a slight transcription of the triglyceride on the support. In the present invention, it has become possible to reduce the amount of triglyceride transferred to a support by adding triglyceride in an emulsified dispersion form, resulting in resolution of the aforementioned slipping. In addition, it has become possible to prevent contamination of a Fuji Dry Chem (FDC), which is a detection element for neutral fat measurement, upon measurement of triglyceride (neutral fat). Also, the stability of an emulsified product has been improved by preparing an emulsified dispersion in a fine particle form. Thus, stable production conditions have been established. Further, it has become possible to significantly reduce aggregation in an application solution comprising an emulsified dispersion by adding a hydrophilic polymer (e.g., hydroxypropyl cellulose or gelatin) to the emulsified dispersion.

BEST MODE FOR CARRYING OUT THE INVENTION

Hereinafter, the present invention will be described more in detail.

The method of the present invention for producing a dry analytical element for measurement of pancreatic lipase contained in a body fluid which contains triglyceride of long chain alkyl fatty acid having 12 to 22 carbon atoms, monoglyceride lipase, and a glycerine measurement reagent, and comprises a water-impermeable support and at least one spreading or reagent layer, is characterized in that said method comprises the step of coating an emulsion/dispersion solution of triglyceride with an average particle size of 1 µm or less.

The average particle size of the emulsified dispersion may be 1 µm or less. However, the average particle size of the emulsified dispersion is preferably 0.5 µm or less, more preferably 0.3 µm or less, and further preferably 0.2 µm or less. As an emulsification method, an ultrasonication method, a shearing method, or a high-pressure homogenization method can be used. In the case of a high-pressure emulsification method, fine dispersion is achieved while foam formation is suppressed. A triolein emulsion/dispersion solution is produced by high-pressure emulsification at a pressure of preferably 100 MPa or more. A combination method of a high-pressure homogenization method and an ultrasonic dispersion method is preferable.

A method of addition of triglyceride serving as a substrate is described below. During the study process of the present invention, it has been found that triglyceride, which is oil, is readily transferred to a support or an analytical element in the case of a method of addition of triglyceride wherein triglyceride is solubilized in an organic solvent such as ethanol. Therefore, the use of this method must be carefully considered. Contamination with triglyceride might spread to the whole production apparatus, making it impossible to carry out delivery at a constant rate. In addition, in the case of the use of a method of addition of triglyceride wherein triglyceride is dissolved in an aqueous solvent by adding a surfactant in a large amount, there might be increases not only in the reactivity of pancreatic lipase but also in the reactivity of nonpancreatic lipase or esterase with such a substrate. Further, a surfactant might deactivate a conjugated enzyme. Thus, this method is also not preferable.

In view of the above, in the present invention, a method of addition of triglyceride to a dry analytical element wherein triglyceride is prepared in the form of an emulsion/dispersion solution, is used. Hitherto, a dispersion method wherein ultrasonic dispersion is carried out with the use of a protective colloid such as gum arabic has been used as a method of addition of triolein to a lipase analysis solution or a dry analytical tool. In this method, the average particle size of a dispersion to be formed generally exceeds 1 µm. In such case, even in consideration of stabilization with the use of a protective colloid, the glyceride particle size becomes unstable depending on the timing of addition of a reagent, agitation efficiency, fluctuations in the solution temperature, and the like. Thus, the glyceride particle size varies in a single lot or different lots. Therefore, it is difficult to produce a dry analytical tool for lipase with good precision. Further, unless the dispersion particle size is reduced, particle reaggregation or sedimentation takes place. Such instability of a dispersion solution is problematic upon production of a uniform analytical element. Thus, the fine dispersion method of the present invention is preferable.

(Emulsification Method)
[High-Pressure Homogenizer]

Glyceride (lipase substrate) such as triolein in the present invention can be emulsified in a fine oil droplet form with the use of a known emulsification method. An emulsification method used in the present invention may comprise the use of a high-pressure homogenizer. Examples of high-pressure homogenizers include a chamber-type high-pressure homogenizer having a chamber in which a treatment solution channel is fixed, and a homogeneous-valve-type high-pressure homogenizer having a homogeneous valve. Of these, a homogeneous-valve-type high-pressure homogenizer has been widely used particularly in the fields of food, cosmetics, and the like, which involve emulsification. This is because such a homogenizer facilitates control of the width of a treatment solution channel such that the pressure and the flow volume during the operation can be arbitrarily predetermined. In addition, such homogenizer can be applied to wide range of operations. On the other hand, when high pressurization is required, a chamber-type high-pressure homogenizer is used in view of ease of design of a pressurizing structure, although the degree of operational freedom is low.

Examples of a chamber-type high-pressure homogenizer include a Microfluidizer (Microfluidics), a Nanomizer (Yoshida Kikai Co., Ltd.), and an Altimizer (Sugino Machine Limited).

Examples of a homogeneous-valve-type high-pressure homogenizer include a Gaulin-type homogenizer (APV), a Rannie-type homogenizer (Rannie), high-pressure homogenizer (Niro Soavi), a homogenizer (Sanwa Engineering Ltd.), a high-pressure homogenizer (Izumi Food Machinery Co., Ltd.), and a super-high-pressure homogenizer (IKA).

In the case of using a high-pressure homogenizer, emulsification is thought to be achieved by the large shearing force generated when liquid passes through a very narrow (small) gap at a high speed. The degree of such shearing force is substantially proportional to the pressure applied. Therefore, a higher pressure results in a larger shearing force to oil droplet particles emulsified in an aqueous liquid (i.e., emulsification force). However, kinetic energy generated due to passage of liquid at a high speed is mainly converted into heat. Thus, a higher pressure results in a higher liquid temperature. This might cause deterioration in the components of an emulsified solution or promotion of recoalescence of particles in the solution. Although a high-pressure homogenizer has an optimum pressure value, the optimum value would vary depending on the substance to be emulsified and target particle size.

In order to achieve emulsification/dispersion of triglyceride at an average particle size of 200 nm or less in the present invention, emulsification is carried out at a pressure of preferably 100 MPa to 300 MPa and more preferably 150 MPa to 300 MPa. Operation at such high pressures can be carried out with the use of a homogeneous-valve-type high-pressure homogenizer. However, in view of the stability of operational conditions, a chamber-type high-pressure homogenizer is more preferable. In the case of a homogeneous-valve-type high-pressure homogenizer, it is difficult to set pressure to 150 MPa in view of the structure. In the case of a laboratory-scale homogenizer, pressure can be increased to approximately 200 MPa. However, in view of stable production, the maximum pressure for operation is 150 MPa. Meanwhile, a chamber-type super-high-pressure homogenizer that can be operated at up to 300 MPa has been realized in a production scale. Therefore, such homogenizer is preferably used as an emulsifying apparatus of the present invention. An emulsified solution is cooled by a kind of cooler within 30 seconds and preferably 3 seconds after liquid passage through the chamber. A sufficiently finely emulsified product can be obtained even with a single cycle of emulsification/cooling. However, in view of fine product formation, a cycle of emulsification/cooling is repeatedly carried out more than once and preferably 3 to 10 times.

[Ultrasonic Homogenizer]

Another effective method of fine emulsification of glyceride in the present invention comprises the use of an ultrasonic homogenizer. Specifically, a method wherein a premix is ultrasonicated at a frequency of 15 to 40 kHz has been known. However, an ultrasonic generator that can carry out irradiation to a sufficient extent is not commercially available. In the case of using a small apparatus, the volume of a liquid medium that can be treated is limited. Therefore, it has been difficult to achieve industrial mass production by a method for producing an emulsified product with the use of such an ultrasonic generator. This is because the volume of a liquid medium that can be treated is small in such case, although an emulsified product prepared in a small volume has very excellent properties.

Recently, it has become possible to achieve mass production to some extent along with progress in high-output apparatuses for ultrasonic irradiation. Examples of a high-output ultrasonic homogenizer include ultrasonic homogenizers US-1200T, RUS-1200T, and MUS-1200T (Nippon Seiki Co., Ltd) and ultrasonic processors UIP2000, UIP-4000, UIP-8000, and UIP-16000 (Hielscher). Fine emulsification has become possible with the use of such a high-output ultrasonic irradiation apparatus at a frequency of 25 kHz or less and preferably 15 to 20 kHz and an energy density of an emulsification portion of 100 W/cm$^2$ or more and preferably 120 W/cm$^2$.

Batch-type ultrasonic irradiation may be carried out. In such case, combined use of an apparatus with a means of agitating the entire emulsified solution is preferable. Such agitation means that can be used is an agitator, a magnetic stirrer, a disper, or the like. Further preferably, flow-type ultrasonic irradiation can be carried out. A flow-type ultrasonic irradiation apparatus refers to an apparatus comprising a tank and a pump for supplying an emulsified solution, in which an emulsified solution is supplied at a constant flow rate to a chamber having an ultrasonic irradiation portion. A solution can be effectively supplied to a chamber from any side of the chamber. However, it is particularly preferable to use a method for supplying a solution to a chamber from the side from which the solution flows in the vertical direction toward the ultrasonic irradiation surface.

The time period for ultrasonic irradiation is not particularly limited. However, it is preferably 2 to 200 minutes for each 1 kg of an emulsified product in terms of the time period during which ultrasonic irradiation is carried out substantially in a container. An excessively short time period would result in insufficient dispersion. An excessively long time period would result in recoalescence. An optimum time period would vary depending on the type of glyceride and the way of using an emulsifier. However, in general, such time period is preferably 10 minutes to 100 minutes/Kg.

An increase in the emulsified solution temperature due to high-energy-density ultrasonic irradiation might result in deterioration in the constituents of an emulsified solution or recoalescence of particles. Thus, it is preferable to use a cooling means with the above apparatus. In the case of batch-type irradiation, it is possible to cool the outer surface of an irradiation container. Alternatively, a cooling unit can be provided inside such a container. Also, in the case of flow-type irradiation, it is preferable to provide a cooling means such as a heat exchanger in the circular-flow path in addition to a means of cooling the outer surface of an ultrasonic irradiation chamber.

Combined use of an ultrasonic homogenizer and the aforementioned super-high-pressure homogenizer results in the obtaining of a further preferable emulsified dispersion. Specifically, emulsification is carried out with a super-high-pressure homogenizer after a premix is subjected to ultrasonic irradiation. Accordingly, emulsification efficiency increases with the use of a super-high-pressure homogenizer, allowing reduction in the number of passes and in the number of bulk molecules. In addition, an emulsified product subjected to dispersion with the use of a super-high-pressure homogenizer is further subjected to ultrasonic irradiation, such that bulk particles disappear, which is preferable. Further, it is also possible to repeat the above steps in an arbitrary order. For instance, super-high-pressure dispersion and ultrasonic irradiation can be alternately carried out. In addition, an excellent emulsified product of triglyceride with a particle size of less than 1 μm can be produced by a shearing method or combined use of an ultrasonic emulsification and a shearing method.

<Particle size measurement method 1>

The average particle size in the present invention is designated as the volume average particle size (Mean Volume Diameter). The particle size of the oil-in-water droplet emulsion of the present invention (volume average particle size) can be determined with the use of a commercially available particle size distribution analyzer, for example. Known examples of a method for determining the emulsion particle size distribution include an optical microscopy method, a confocal scanning laser microscopy method, an electron microscopy method, an atomic force microscopy method, a static light scattering method, a laser diffraction method, a dynamic light scattering method, a centrifugal sedimentation method, an electropulse measurement method, a chromatography method, and an ultrasonic attenuation method. Apparatuses based on the principles of the respective methods are commercially available.

In view of the particle size range and ease of measurement in the present invention, a dynamic light scattering method is preferable as a method for measuring the emulsion particle size of the present invention. Examples of a commercially available measurement apparatus using a dynamic light scattering method include Nanotrack UPA (Nikkiso, Co., Ltd.), a dynamic-light-scattering-type particle size distribution analyzer LB-550 (HORIBA, Ltd.), and a fiber-optics particle size analyzer FPAR-1000 (Otsuka Electronics Co., Ltd.).

In addition, the particle size of an emulsion composition can be adjusted based on factors such as agitation conditions (shearing force/temperature/pressure) in the production method and the proportion of an oil phase to a water phase, in addition to the components of the emulsion composition.

The particle size in the present invention was measured at 25° C. with the use of Nanotrack UPA-EX150 (Nikkiso, Co., Ltd.). Then, the particle size and the degree of monodispersity were evaluated. The particle size was evaluated based on the volume average particle size "Mv." The degree of monodispersity was evaluated based on the value (Mv/Mn) obtained by dividing the volume average particle size "Mv" by the number average particle size "Mn."

In a method for measuring the above volume average particle size, dilution is carried out with pure water such that the oil phase constituent concentration becomes 0.1 to 1% by weight, and the resultant is introduced into a measurement cell portion. The volume average particle size can be obtained with the use of a dispersion medium refraction index of 1.3313 (pure water) and a dispersion medium viscosity of 0.8846 mPa·S (pure water).

In addition, there is a simple particle size measurement method wherein the average particle size (corresponding to "the average differential cross section" in this method) is calculated with the turbidity ratio obtained based on the Mie scattering theory (R. J. Gledhill, J. Phys. Chem., [66] 458

(1962)). The scattering intensity in the Mie scattering range is determined depending on the wavelength raised to the n-th power. Since "n" is determined depending on the particle size, wavelength dependency is resolved when the particle size exceeds the above range. On the other hand, when the particle size is below the same, the scattering intensity is inversely proportional to the wavelength raised to the $4^{th}$ power, regardless of the particle size, which is within the range of so-called Rayleigh scattering.

<Hydrophilic Polymer Added to a Spreading Layer>

A spreading layer may contain a hydrophilic polymer. Examples of a hydrophilic polymer include starch, cellulose and cellulose derivatives (e.g., methylcellulose, hydroxyethyl cellulose, and hydroxypropyl cellulose), agarose, gelatins (e.g., acid-treated gelatin and deionized gelatin), gelatin derivatives (e.g., phthalated gelatin and hydroxy-acrylate-grafted gelatin), acrylamide polymers, copolymers of acrylamide and various vinyl monomer, vinyl pyrrolidone polymers, copolymers of vinyl pyrrolidone and various vinyl monomer, acrylate polymers, and copolymers of acrylate and various vinyl monomer. Among the above hydrophilic polymers, vinyl pyrrolidone derivatives and cellulose derivatives are preferable. Cellulose derivatives are particularly preferable. This is because, when peroxidase and leuco dye are contained in a glycerine measurement reagent used in the present invention, polyvinyl pyrrolidone is likely to cause non-specific color development.

<A Water-Soluble Polymer Added to a Triglyceride Emulsion/Dispersion Solution>

In particular, a hydrophilic polymer to be added to a spreading layer is preferably added to a triglyceride emulsion/dispersion solution for suppression of transfer of triglyceride. Examples of particularly preferable hydrophilic polymers include polyvinyl pyrrolidone, polyacrylamide, cellulose derivatives, and gelatin. Preferably, a cellulose derivative is selected from the group consisting of hydroxypropyl cellulose, hydroxyethyl cellulose, and methylcellulose. Examples of a further preferable hydrophilic polymer include hydroxypropyl cellulose and gelatin. The amount of a hydrophilic polymer added to a triglyceride emulsion/dispersion solution is preferably 5 g/m$^2$ or more and more preferably 10 g/m$^2$ or more in terms of the total amount of hydrophilic polymer.

According to the present invention, a triolein emulsion/dispersion solution was allowed to contain gelatin. Accordingly, preferable results were obtained regarding preservation properties of a triolein emulsified dispersion, which is a starting material for production. Specifically, a triolein emulsion/dispersion solution was stable in a dissolved state for at least 6 hours. Besides, since gelatin has the property of being gelatinized at room temperature or lower, a triolein emulsified dispersion or the solution thereof was cold-stored so as to be preserved for long time. It was considered that this was because the dispersion in a liquid form when heated was gelatinized during cold storage, and thus reaggregation of triolein was suppressed. In order to improve long-term stability of an emulsified dispersion containing gelatin, a preservative can be added. Based on the above production techniques, cold storage of a triolein emulsified dispersion has been realized for at least 2 weeks. Examples of gelatin that can be used include acid-treated gelatin and alkali-treated gelatin. Alkali-treated gelatin is preferable.

<Triglyceride>

In order to improve specificity to pancreatic lipase, the triglyceride used in the present invention is a triglyceride of long chain alkyl chain fatty acid. The long chain alkyl chain may be saturated or unsaturated. An unsaturated fatty acid triglyceride is preferable. The reactivity of unsaturated fatty acid with pancreatic lipase is relatively low. In terms of selectivity for pancreatic lipase, the alkyl chain length of the long chain alkyl chain fatty acid may be 12 to 22 carbon atoms, and it may be preferably 16 to 20 carbon atoms. Several examples will be given below.

Examples of saturated fatty acids include lauric acid ($C_{12:0}$), myristic acid ($C_{14:0}$), palmitic acid ($C_{16:0}$), stearic acid ($C_{18:0}$), arachic acid ($C_{20:0}$), and behenic acid ($C_{22:0}$). Examples of unsaturated fatty acids include palmitoleic acid ($C_{16:1}$), petroselinic acid ($C_{11}H_{23}COOH$), oleic acid ($C_{18:1}$), linolic acid ($C_{18:1}$), linolenic acid ($C_{18:2}$), eleostearic acid ($C_{18:3}$), and arachidonic acid ($C_{20:4}$). Among them, unsaturated fatty acid triglyceride is preferable. Triglycerides of oleic acid and linolic acid are preferable. A particularly preferred triglyceride is triolein, which is a triglyceride of oleic acid.

<Monoglyceride Lipase>

Monoglyceride lipase is added to a reagent system that is incorporated into the dry analytical element of the present invention. A preferred example of monoglyceride lipase is one that does not substantially react with triglyceride and diglyceride but reacts with monoglyceride of long chain fatty acid. *Bacillus stearothermophilus* H-165-derived monoglyceride lipase described in JP Patent Publication (Kokai) No. 63-245672 A (1988) and JP Patent Publication (Kokai) No. 4-316500 A (1992) is particularly preferable.

<Glycerin Measurement Reagent>

In the measurement reaction system used in the present invention, monoglyceride generated by degradation of triglyceride used as a substrate with lipase as a measurement target is decomposed with monoglyceride lipase. In a preferred glycerin coloring system, L-α-glycerophosphate is obtained from the resulting glycerol with the use of glycerol kinase. Then, L-α-glycerophosphate is turned into dihydroxyacetone phosphate with L-α-glycerophosphate oxidase, and hydrogen peroxide is generated. Coloring from a coloring dye is induced by the function of peroxidase with the use of hydrogen peroxide.

Glycerol kinase allows glycerol and ATP to react with each other so as to change them into L-α-glycerophosphate (L-glycerol-3-phosphate) and ADP, respectively. It uses coenzymes such as $Mg^{2+}$ and $Mn^{2+}$.

L-α-glycerophosphate oxidase (glycerol-3-phosphate oxidase) oxidizes L-glycerophosphate so as to change it into dihydroxyacetone phosphate and generate hydrogen peroxide.

Various coloring systems in which coloring is caused by the function of peroxidase with the use of hydrogen peroxide have been developed for dry analytical elements. Thus, it is possible to appropriately select and use one thereof. Most of them are leuco dyes represented by o-toluidine.

<Layer Structure>

As a layer structure, the dry analytical element of the present invention comprises at least one spreading layer or reagent layer, and a support which is used to further enhance measurement accuracy and strength and to improve transporting ability during a production process. In the simplest form, the layer consists of support and a spreading layer having the functions as a reagent layer. The number of such layers may be increased.

<Support>

A light-permeable and water-impermeable support can be used to constitute a support layer of the dry analytical element for lipase measurement of the present invention. When measurement is conducted from the spreading layer side, a light-impermeable support may be used. The support gives strength to the dry analytical element and improves the production efficiency. An example of a light-permeable/water-impermeable support is a film- or sheet-type transparent support having a thickness of approximately 50 μm to 1 mm and preferably approximately 80 μm to 300 μm and comprising polymers such as polyethylene terephthalate, polycarbonate of bisphenol A, polystyrene, cellulose ester (e.g., cellulose diacetate, cellulose triacetate, or cellulose acetate propionate). In terms of strength and optical properties, a preferred material is polyethylene terephthalate.

An undercoat layer is provided on the surface of a support, as necessary, such that adhesion between a reaction layer provided on the support and the support can be strengthened. In addition, physical or chemical activation treatment is carried out on the support surface, instead of provision of an undercoat layer, such that adhesivity can be improved.

<Reagent Layer>

A reagent layer may be provided on a support (via another layer such as an undercoat layer in some cases). A reagent layer is a water-absorbing and water-permeable layer containing a hydrophilic polymer binder in which at least a portion of a reagent composition described below, such composition reacting with lipase serving as an analyte so as to cause optically detectable changes, is substantially uniformly dispersed.

A hydrophilic polymer that can be used as a binder for a reaction layer is generally a natural or synthetic hydrophilic polymer having a swelling rate upon water absorption at 30° C. in the range of approximately 150% to 2000% and preferably of approximately 250% to 1500%. Examples of such hydrophilic polymer include gelatins (e.g., acid-treated gelatin and deionized gelatin), gelatin derivatives (e.g., phthalated gelatin and hydroxyacrylate graft gelatin), agarose, pullulan, pullulan derivatives, polyacrylamide, polyvinyl alcohol, and polyvinylpyrrolidone, which are disclosed in JP Patent Publication (Kokai) No. 58-171864 A (1983), JP Patent Publication (Kokai) No. 60-108753 A (1985), and the like.

A reagent layer may be a layer that has been appropriately cross-linked and cured using a crosslinking agent. Examples of a crosslinking agent include: conventional vinyl sulfone crosslinking agents such as 1,2-bis(vinyl sulfonylacetamide) ethane and bis(vinyl sulfonylmethyl)ether; aldehyde and the like for gelatin; and aldehyde and epoxy compounds comprising two glycidyl groups and the like for a methallyl alcohol copolymer.

The thickness of a reagent layer when dried is preferably in the range of approximately 1 μm to 100 μm and more preferably of approximately 3 μm to 30 μm. Preferably, a reagent layer is substantially transparent.

<Spreading Layer>

According to the present invention, it is preferable to use a fabric spreading layer as a porous spreading layer. Alternatively, it is also possible to use a non-fabric material such as a porous membrane of polysulfone or acetylcellulose, porous membrane formed with microbeads, glass fiber filter paper, or filter paper.

<Fabric>

Examples of the porous spreading layer of fabric include woven fabric spreading layers (e.g., plain weave fabric such as broadcloth or poplin) described in JP Patent Publication (Kokai) No. 55-164356 A (1980), JP Patent Publication (Kokai) No. 57-66359 A (1982), and the like; knitted fabric spreading layers (e.g., tricot knitted fabric, double tricot knitted fabric, and Milanese knitted fabric) described in JP Patent Publication (Kokai) No. 60-222769 A (1985) and the like; and a spreading layer comprising woven fabric or knitted fabric subjected to etching treatment with an alkaline etching solution described in JP Patent Publication (Kokai) No. 1-172753 A (1989). Knitted fabric is preferable. In particular, tricot knitted fabric is preferable. Examples of fabric material used include polyester, cotton, nylon, silk, vinylon, rayon, polyamide, acrylic, wool, polypropylene, and hemp. Preferably, polyester is used. The appropriate thickness of the spreading layer is approximately 50 to 400 μm and preferably approximately 200 to 400 μm. The porosity of fabric is approximately 20% to 90% and preferably approximately 40% to 85%.

In the cases of woven fabric and knitted fabric used for a porous spreading layer, it is possible to improve the adhesivity of such fabric to a lower layer (close to a support) by carrying out a physical activation treatment represented by a glow discharge treatment or corona discharge treatment disclosed in JP Patent Publication (Kokai) No. 57-66359 A (1982) on at least one side of the fabric or by hydrophilizing the fabric in a manner such that a washing and degreasing treatment and/or a hydrophilization treatment involving surfactant impregnation, hydrophilic polymer impregnation, or the like, which are disclosed in JP Patent Publication (Kokai) No. 55-164356 A (1980), JP Patent Publication (Kokai) No. 57-66359 A (1982) and the like, are carried out, or such that a treatment involving an appropriate combination of the above treatments is carried out in a sequential manner.

When a porous layer is used as a spreading reaction layer, a porous medium thereof may be fibrous or nonfibrous. Examples of a fibrous material that can be used include filter paper, nonwoven fabric, woven fabric (e.g., plain weave fabric), knitted fabric (e.g., tricot knitted fabric), and glass fiber filter paper. Examples of a nonfibrous material include a membrane filter comprising cellulose acetate and the like disclosed in JP Patent Publication (Kokai) No. 49-53888 A (1974), and a particulate unit layer having continuous voids, such layer comprising fine particles of an inorganic or organic substance disclosed in JP Patent Publication (Kokai) No. 49-53888 A (1974), JP Patent Publication (Kokai) No. 55-90859 A (1980) (corresponding to U.S. Pat. No. 4,258,001), JP Patent Publication (Kokai) No. 58-70163 A (1983) (corresponding to U.S. Pat. No. 4,486,537), and the like. Also, layer laminated products having a plurality of porous layers that partially adhere to each other disclosed in the following documents and the like are preferable: JP Patent Publication (Kokai) No. 61-4959 A (1986) (corresponding to EP 0166365 A); JP Patent Publication (Kokai) No. 62-116258 A (1987); JP Patent Publication (Kokai) No. 62-138756 A (1987) (corresponding to EP 0226465 A); JP Patent Publication (Kokai) No. 62-138757 A (1987) (corresponding to EP 0226465 A); and JP Patent Publication (Kokai) No. 62-138758 A (1987) (corresponding to EP 0226465 A).

In order to add a reagent to a spreading layer, a spreading layer is first formed and then a reaction reagent may be added by means of coating or the like. Alternatively, an example of a useful method is the method comprising impregnating a porous membrane or the like composed of paper, fabric, a polymer, or the like with the reagent of the present invention or coating the reagent thereto and allowing the resultant to adhere to another water-permeable layer formed on a support as described in JP Patent Publication (Kokai) No. 55-164356 A (1980).

A porous layer may be a spreading layer having a so-called measuring function that allows a supplied liquid to be developed in an area that is almost in proportion to the amount of the liquid. It is effective to control such function with the use of a surfactant and a hydrophilic binder.

It is also possible to provide a layer that differs from the above layers to the dry analytical element of the present invention. Examples thereof include a light-shielding layer, a water-absorbing layer, and an adhesive layer.

In order to increase the reactivity of pancreatic lipase mainly contained in blood that serves as a measurement target of the present invention, as a reagent to be incorporated into the dry analytical element of the present invention, colipase is preferably added to the reagent system of the present invention. A preferred example of such colipase is pig-pancreas-derived colipase. In addition, in order to increase the activity of pancreatic lipase and to reduce the lipase activity of non-pancreatic lipase, deoxycholic acid or taurocholic acid is added as an activating agent. Thus, influences of esterase, liver lipase, and lipoprotein lipase are removed, and thus pancreatic lipase can be measured with high specificity.

The contents of the above reagents are as follows: triglyceride: approximately 0.1 to 15 $g/m^2$ and preferably approximately 0.5 to 10 $g/m^2$; glycerol kinase: 0.5 to 100 $KU/m^2$ and preferably approximately 1 to 10 $KU/m^2$; L-$\alpha$-glycerophosphate oxidase: approximately 2 to 200 $KU/m^2$ and preferably approximately 1 to 30 $KU/m^2$; peroxidase: approximately 1 to 200 $KU/m^2$ and preferably approximately 1 to 50 $KU/m^2$; a coloring dye: approximately 0.05 to 2.00 $g/m^2$ and preferably approximately 0.1 to 1.00 $g/m^2$; colipase: preferably 0.010 to 0.400 $g/m^2$, deoxycholic acid: approximately 0.1 to 10 $g/m^2$; taurodeoxycholic acid: approximately 0.05 to 10 $g/m^2$.

Monoglyceride lipase used herein is in an amount of preferably 8000 $U/m^2$ to 1000 $U/m^2$, more preferably 5000 $U/m^2$ to 2000 $U/m^2$. Although monoglyceride lipase is a conjugated enzyme, it is not preferable to add it in an excessive amount. When diglyceride is used as a substrate, the background level might be increased. In addition, even when triglyceride is used as a substrate, the reaction of a part of lipoprotein in blood is induced along with increases in the amount of monoglyceride lipase, resulting in the generation of measurement errors.

All of the reagent composition may be contained in a reaction layer or spreading layer. Alternatively, it may be divided such that it is contained in both layers, or it may be partially contained in another layer.

It is also possible to add other reagents, such as a buffer and a surfactant, to the dry analytical element of the present invention.

Examples of a buffer that can be contained in the dry analytical element of the present invention include known buffers such as a carbonate buffer, a borate buffer, a phosphate buffer, a tris salt buffer, and a Good's buffer. These buffers can be selected and used by referring to known references such as "Primary Experimental Methods for Proteins and Enzymes (*Tanpakushitsu/Koso no Kiso Jikken-hou*)" (Takeichi Kajio et al., Nankodo Co., Ltd., 1981). The content thereof may be approximately equal to that generally used in an integrated multilayer analytical element, which is in the range of approximately 100 $mg/m^2$ to 20 $g/m^2$ and preferably of approximately 1 $g/m^2$ to 10 $g/m^2$.

In the case of analysis using a dry analytical element, the analysis is carried out without diluting a specimen. Thus, the analysis is easily affected by various ingredients contained in the specimen. In order to solve such problem regarding a difference in such lipase activation among specimens, addition of alkylphenylsulfonate such as sodium dodecylbenzenesulfonate was found to be useful. That is to say, in analyses using the conventional dry analytical elements, poor multi-specimen correlation was provided due to poor lipase reactions of several specimens. In order to solve this problem, alkylphenylsulfonate such as sodium dodecylbenzenesulfonate was added to a dry analytical element, so as to succeed in significantly improving a correlation coefficient. This result was obtained because the lipase activity of specimens having negative errors in the correlation was recovered.

Examples of an anionic surfactant used in the present invention include those having a carboxyl group, a sulfonic acid group, a sulfate group or a phosphate as a hydrophilic group. Preferred anionic surfactants having a sulfonic acid group that can be used in the present invention include alkylbenzenesulfonate, alkylnaphthalenesulfonate, alkylsulfate, a polyoxyethylene alkyl ether sulfate, $\alpha$-olefin sulfonate, and N-acylmethyl taurine salts. The number of carbon atoms of a hydrophobic group is preferably approximately 12 to 20. Among others, those that do not inhibit lipase activity and do not deactivate enzyme added to the dry analytical element are preferable.

Among these anionic surfactants, alkylbenzenesulfonate is preferable, and alkylbenzenesulfonate having an alkyl chain containing 10 to 14 carbon atoms is more preferable. Moreover, straight-chain dodecylbenzenesulfonate containing 12 carbon atoms, which is a main component of detergent, is further preferable. As salts, sodium salts are preferable. However, potassium salts or lithium salts may also be used. It may also be possible to form salts in the dry analytical element after addition of alkylbenzenesulfonate.

As an anionic surfactant having a carboxy group, bile salts having action to activate lipase are preferable. Preferred examples include deoxycholate, cholate, taurocholate, taurodeoxycholate, and deoxytaurocholate. Particularly preferred examples include sodium deoxycholate and sodium talurodeoxycholate.

The optimal combination of anionic surfactants is sodium deoxycholate, sodium taurodeoxycholate, and straight-chain dodecylbenzenesulfonate.

The additive amount of alkylphenylsulfonate in the present invention is not particularly limited, as long as the effect of the present invention can be achieved. The additive amount of alkylphenylsulfonate is preferably 0.1 to 10 $g/m^2$, more preferably 0.2 to 5 $g/m^2$, and further preferably 0.5 to 5 $g/m^2$.

The reagent layer or spreading layer of the analytical element of the present invention may also comprise surfactants other than the aforementioned anionic surfactant, such as a nonionic surfactant. A surfactant used contains a combination of a lipophilic group such as an alkyl group, an alkylphenyl group, a styrenated phenyl group, a benzilphenyl group or a sorbitanalkyl group, with a hydrophilic group such as a polyoxyethylene group, a polyglycerol group or a polyoxyethylenepolypropylene polymer. Examples of such surfactant include polyoxyethylene alkylether, polyoxyethylene branched alkylether, polyoxyalkylene alkylether, polyoxyethylene alkylphenylether, and alkylphenyl polyglyceride. Specific examples thereof include polyoxyethylene tridecylether, polyoxyethylene branched decylether, polyoxyethylene p-octylphenyl ether, polyoxyethylene p-octylphenyl ether, polyoxyethylene p-nonylphenyl ether, polyoxyethylene oleyl ether, polyoxyethylene sorbitan monolaurate, p-nonylphenoxypolyglycidol, and octylglucoside. Among such nonionic surfactants, polyoxyethylene tridecylether, polyoxyethylene branched decylether, p-octylphenoxypolyethoxyethanol, p-nonylphenoxypolyethoxyethanol, p-nonylphenoxypolyglycidol, and the like are preferable. By adding a nonionic surfactant in a spreading layer, a function of developing an aqueous liquid sample (metering function) is further improved. By adding a nonionic surfactant in a reaction layer, water contained in an aqueous liquid sample is facilitated to be absorbed to a reaction layer in a substantially uniform manner upon analysis operations. Also in such case, the liquid comes into contact with a spreading layer in a rapid and substantially uniform manner.

A method for producing the dry analytical element of the present invention will be described. A binder such as gelatin and a surfactant are added to a support. A water-soluble coating solution having improved film-forming properties is coated thereto and dried, and thus a reagent layer is prepared. To the reagent layer, peroxidase and leuco dye used as coloring reagents, and as necessary, ATP, magnesium chloride, and a pH buffer may be added. In addition, when gelatin is used as a binder, a so-called hardening agent may be added in order to crosslink the gelatin. With regard to a spreading layer, when fabric or a formed porous membrane is used as a spreading layer, for example, water is added to a reagent layer such that a part thereof is solubilized. Thereafter, a binder is further softened by heating, as necessary, and it is then fixed by applying pressure to a spreading layer membrane and a reagent layer on the support, followed by drying.

(Method for Preparing Triglyceride Solution)

A hydrophilic polymer may be added to the emulsion/dispersion solution of triglyceride in order to increase the temporal stability of the addition solution. In order to increase coating stability, a surfactant may be added to optimize dynamic/static surface tension. As such a surfactant, a nonionic surfactant is often used. An anionic surfactant may also be used, when it has only little effect on coupled enzyme to be added.

(Coating/Drying Methods)

Among methods of adding reagents such as triglyceride, there is a highly efficient production method comprising a step of using a Giesser device for uniform coating and drying. In such step, drying is preferably hot-air drying. Drying air is at a temperature of preferably 20° C. to 60° C. and particularly preferably 25° C. to 40° C. Preferably, a dew point is 0° C. to 10° C. Preferably, an air flow is 0.5 to 10 m/second. A required time period for drying is a time period during which a solvent is substantially dried. Meanwhile, drying for a long period of time may result in deactivation of a conjugated enzyme, and thus the time period for drying is preferably 1 to 60 minutes. It is also possible to predetermine preferable drying conditions by setting the temperature, dew point, air speed, and direction of drying air and a time period for drying in each of a plurality of drying zones.

Other reagents necessary for the measurement of lipase activity are preferably prepared, separately from preparation of an additive solution of triglyceride. An anionic surfactant acting as a lipase activator, such as deoxycholate or taurodeoxycholate, colipase, coupled enzyme monoglyceride lipase, and a pH buffer are dissolved in distilled water. In order to improve coating compatibility and blood-developing ability, a binder and a surfactant may be added. $CaCl_2$ may be added to any coating solution. However, it may react with deoxycholic acid so as to form an aggregate in some cases. Thus, it is preferable to dissolve $CaCl_2$ in a substrate solution for addition. The pH is preferably adjusted to pH 7 to 9, which is close to the optimal pH of pancreatic lipase. Basically, each reaction reagent may be added to any layer upon production, provided that reagent conditions appropriate for reaction can be determined upon reaction of lipase in a specimen via dissolution and dispersion. The reaction reagent solution may also be added to the spreading layer by the aforementioned coating/drying methods.

Regarding a method for adding a reagent, impregnation or spraying may be carried out, as long as a uniform amount of a reagent can be determined. Regarding the order of preparation of individual layers, a method whereby a uniform layer in which a reagent is not degraded is obtained may be used.

In view of production, packaging, transportation, storage, measurement operations, and other points, it is preferable to use the integrated multilayer analytical element of the present invention in a manner such that it is cut into square pieces having sides each approximately 10 mm to 30 mm in length or circular pieces having sizes similar to the sizes of the square pieces, following which the pieces are accommodated in slide frames or the like disclosed in the following documents so as to be used as analytical slides: JP Patent Publication (Kokai) No. 57-63452 A (1982); JP Patent Publication (Kokai) No. 54-156079 A (1979); JP Utility Model Publication (Kokai) No. 56-142454 U (1981); JP Utility Model Publication (Kokai) No. 58-32350 U (1983); and JP Patent Publication (Kokai) No. 58-501144 A (1983).

The integrated multilayer analytical element of the present invention is used as follows. An aqueous liquid sample in an amount of approximately 5 µl to 30 µl, and preferably approximately 8 µl to 15 µl, is supplied by spotting to a porous spreading layer according to the methods according to the above documents. If necessary, incubation is carried out at a substantially constant temperature in the range of approximately 20° C. to 45° C. Then, reflective photometry is carried out from the light-permeable support side of the integrated multilayer analytical element in order to observe detectable changes therein, including color change and coloring. Thereafter, the target components to be measured in a liquid sample are analyzed based on the principles of colorimetric methods.

In the present invention, the body fluids of a dog, a cat, or other animals may be used. Otherwise, a human body fluid may also be used.

The present invention is hereafter described in greater detail with reference to the following examples, although the technical scope of the present invention is not limited thereto.

EXAMPLES

Comparative Example 1

Production of a Pancreatic Lipase Analytical Slide (by Dissolving Triolein in an Organic Solvent Such that Triolein Forms an Oil Membrane in a Slide)

(Transfer of triolein to a support or a different slide (contamination) is most possibly observed in the rolling-up step involving "addition of a substrate." Thus, in the triolein transfer experiment, a substrate-applied product obtained after "addition of a substrate" (at which transfer of triolein is most possibly observed) was used.)

(1) Addition of a Glycerine Coloring Reagent:

A reagent to be added was coated as an aqueous solution at a volume of 127 g/m$^2$ (at which the aqueous solution had the composition described below in terms of dry weight for coating) to a gelatin-undercoated polyethylene terephthalate film (180 µm in thickness) which was smooth, colorless and transparent, followed by drying. Subsequently, water was uniformly supplied to the film such that the film became wet. Tricot knitted fabric prepared by knitting (36 gauge) with polyethylene terephthalate spun yarn (corresponding to 50 deniers) or porous membrane (acetyl cellulose) was laminated thereon via light pressurization. The gelatin was solidified at a drying temperature of 20° C., followed by drying at 45° C. In addition, the coating solution comprising a pH buffer (PIPES) used was adjusted to have a pH of 5.5 with a 1 N—NaOH aqueous solution.

750 gelatin (Nitta Gelatin Inc.): 12 g/m$^2$
PIPES (Dojindo Laboratories): 1.5 g/m$^2$
Magnesium chloride (Wako Pure Chemical Industries, Ltd.): 0.52 g/m$^2$
ATP-2 sodium chloride (Oriental Yeast Co., Ltd.): 1.4 g/m$^2$
Polyoxyethylene tridecylether HLB14.8 (Dai-ichi Kogyo Seiyaku Co., Ltd.): 0.3 g/m$^2$
Polyethylene alkyl branched decylether HLB15.9: 0.06 g/m$^2$ (Dai-ichi Kogyo Seiyaku Co., Ltd.)

Leuco dye: 0.21 g/m$^2$
Horseradish peroxidase (TOYOBO Co., Ltd): 14 KU/m$^2$
Glycerol kinase (Asahi Kasei Corporation): 3.8 KU/m$^2$
L-α-glycerophosphate oxidase (Asahi Kasei Corporation): 19 KU/m$^2$
1,2-bis(vinylsulfonylacetamide) ethane: 0.12 g/m$^2$
(2) Addition of a substrate:

A reagent of the composition described below was dissolved in ethanol and coated to the above fabric, followed by hot-air drying at a drying temperature of 32° C. with the use of air at a dew point of 0° C. The ethanol solution was coated at a volume of 220 g/m$^2$ at which the solution had the following composition in terms of dry weight for coating.
Calcium chloride (Wako Pure Chemical Industries, Ltd.): 0.18 g/m$^2$
Polyvinyl pyrrolidone K90 (BASF): 2.0 g/m$^2$
Triolein (95%, MP Biomedicals): 1.1 g/m$^2$
(3) Addition of a lipase reaction supporting agent:

Further, the following reagent was dissolved in water and coated at a volume of 145 g/m$^2$ to the above resultant, followed by drying. Thus, a dry analytical element for pancreatic lipase was prepared. In addition, the coating solution comprising a pH buffer (HEPES) was adjusted to have a pH of 8.0 with the use of a 1 N—NaOH aqueous solution. The composition in terms of dry weight for coating was as follows.
HEPES (Dojindo Laboratories): 6.1 g/m$^2$
Sodium linear dodecylbenzene sulfonate: 1.0 g/m$^2$
(Wako Pure Chemical Industries, Ltd.)
Sodium deoxycholic acid (Wako Pure Chemical Industries, Ltd.): 4.6 g/m$^2$
Sodium taurodeoxycholic acid: 1.5 g/m$^2$
Metolose: 2.1 g/m$^2$
Monoglyceride lipase (Asahi Kasei Corporation): 4400 U/m$^2$
Pig colipase (Roche): 0.1 g/m$^2$
Ascorbate oxidase (TOYOBO Co., Ltd): 8500 U/m$^2$ Comparative Example 2

Emulsification/Dispersion Method of Triolein with a Large Particle Size

Triolein (95%, MP Biomedicals) (1.43 g) was added to an aqueous solution (50 g) containing 10% gum arabic (Wako Pure Chemical Industries, Ltd.), followed by ultrasonic dispersion.

The volume average particle size of triolein in the obtained emulsified product was measured with Nanotrack UPA (Nikkiso, Co., Ltd.) which is a dynamic light scattering particle size distribution analyzer. The particle size was found to be 1.693 μm. The resulting dispersion was allowed to stand at room temperature. As a result, reaggregation of triolein was observed in the emulsified dispersion within 1 hour.

Example 1-1

Fine Emulsification/Dispersion Method of Triolein with a Super-High-Pressure Homogenizer Polyvinyl pyrrolidone K90 (BASF) (4.0 g), gelatin (Nitta Gelatin Inc.) (6.0 g), and sodium linear dodecylbenzene sulfonate (Wako Pure Chemical Industries, Ltd.) (0.5 g) were dissolved in purified water (175 ml) at 60° C. for 30 minutes. Then, the solution temperature was decreased to 40° C. Triolein (95%, MP Biomedicals) (5.0 g) was added to the obtained aqueous solution with agitation. The above coarse dispersion of an oil and water mixture solution was treated with a ultrasonic homogenizer US-600T (Nippon Seiki Co., Ltd) for 3 minutes such that further dispersion was achieved therein. Then, the resultant was further treated 5 times with a Starburst Mini super-high-pressure homogenizer (Sugino Machine Limited) at a pressure of 245 MPa such that fine emulsification was achieved therein.

The volume average particle size of triolein in the obtained emulsified product was measured with Nanotrack UPA (Nikkiso, Co., Ltd.) which is a dynamic light scattering particle size distribution analyzer. The particle size was found to be 190 nm. The obtained dispersion was allowed to stand at 40° C. Thereafter, the dispersion remained stable for 24 hours. In addition, the dispersion remained stable when stored at 4° C. for 2 weeks.

Example 1-2

Fine Emulsification/Dispersion Method of Triolein with a PHYSCOTRON Emulsifying Apparatus Polyvinyl pyrrolidone K90 (BASF) (10.0 g), gelatin (Nitta Gelatin Inc.) (15.0 g), and sodium linear dodecylbenzene sulfonate (Wako Pure Chemical Industries, Ltd.) (1.25 g) were dissolved in purified water (223.5 ml) at 50° C. for 30 minutes. Then, the solution temperature was decreased to 40° C. Triolein (95%, MP Biomedicals) (12.5 g) was added to the obtained aqueous solution with agitation. The above coarse dispersion of an oil and water mixture solution was treated with a PHYSCOTRON emulsifying apparatus (Microtec-nition) at 8000 rpm for 14 minutes and at 12000 rpm for 11 minutes such that fine emulsification was achieved therein.

The volume average particle size of triolein in the obtained emulsified product was measured with Nanotrack UPA (Nikkiso, Co., Ltd.) which is a dynamic light scattering particle size distribution analyzer. The particle size was found to be 370 nm. The obtained dispersion was allowed to stand at 40° C. Thereafter, the dispersion remained stable for 6 hours. In addition, the dispersion remained stable when stored at 4° C. for 2 weeks.

Example 1-3

Fine Emulsification/Dispersion Method of Triolein with a T.K.HOMODISPER f-Model

Polyvinyl pyrrolidone K90 (BASF) (10.0 g), gelatin (Nitta Gelatin Inc.) (15.0 g), and sodium linear dodecylbenzene sulfonate (Wako Pure Chemical Industries, Ltd.) (1.25 g) were dissolved in purified water (223.5 ml) at 50° C. for 30 minutes. Then, the solution temperature was decreased to 40° C. Triolein (95%, MP Biomedicals) (12.5 g) was added to the obtained aqueous solution with agitation. The above coarse dispersion of an oil and water mixture solution was treated with T. K. HOMODISPER f-model (Tokushu Kika Kogyo) at 6000 rpm for 20 minutes such that further dispersion was achieved therein for fine emulsification. The volume average particle size of triolein in the obtained emulsified product was measured with Nanotrack UPA (Nikkiso, Co., Ltd.) which is a dynamic light scattering particle size distribution analyzer. The particle size was found to be 700 nm. The obtained dispersion was allowed to stand at 40° C. Thereafter, the dispersion remained stable for 6 hours. In addition, the dispersion remained stable when stored at 4° C. for 2 weeks.

Example 2

Method of Addition of a Triolein Emulsified Dispersion to a Dry Analytical Element for Lipase Measurement Example 2-1

This Example was carried out as in Comparative Example 1, except that the triolein emulsion/dispersion solution prepared in Example 1-1 to 1-3 was added as a substrate (described below). The emulsification/dispersion solution was coated at a volume of 134 g/m² in view of the stability at the coating step. The composition in terms of dry weight for coating was as follows. The other conditions were the same as those used in Comparative Example 1, and a fabric was used as a developing layer.

Example 2-2

This Example was carried out as in Example 2-1, except that a porous membrane (acetyl cellulose) was used as a developing layer.
Polyvinyl pyrrolidone K90 (BASF): 1.96 g/m²
Calcium chloride (anhydrous) (Wako Pure Chemical Industries, Ltd.): 0.18 g/m²
Triolein emulsion/dispersion solution of Example 1 (with the following formulation in terms of weight for coating)
    Polyvinyl pyrrolidone K90 (BASF): 0.9 g/m²
    750 gelatin (Nitta Gelatin Inc.): 1.3 g/m²
    Triolein (95%, MP Biomedicals): 1.1 g/m²
    Sodium linear dodecylbenzene sulfonate (Wako Pure Chemical Industries, Ltd.): 0.11 g/m²

Example 3

Method for Addition of a Triolein Emulsified Dispersion Containing a Hydrophilic Polymer to a Dry Analytical Element for Lipase Measurement Example 3-1

This Example was carried out as in Comparative Example 1, except that the triolein emulsion/dispersion solution prepared in Example 1-1 to 1-3 was added as a substrate (described below). The emulsification/dispersion solution was coated at a volume of 134 g/m² in view of the stability at the coating step. The composition in terms of dry weight for coating was as follows. The other conditions were the same as those used in Comparative Example 1, and a fabric was used as a developing layer.

Example 3-2

This Example was carried out as in Example 3-1, except that a porous membrane (acetyl cellulose) was used as a developing layer.
Hydroxypropyl cellulose L (Nippon Soda Co., Ltd.): 9.8 g/m²
Calcium chloride (anhydrous) (Wako Pure Chemical Industries, Ltd.): 0.18 g/m²
Triolein emulsion/dispersion solution of Example 1 (with the following formulation in terms of weight for coating)
Polyvinyl pyrrolidone K90 (BASF): 0.9 g/m²
750 gelatin (Nitta Gelatin Inc.): 1.3 g/m²
Triolein (95%, MP Biomedicals): 1.1 g/m²
Sodium linear dodecylbenzene sulfonate (Wako Pure Chemical Industries, Ltd.): 0.11 g/m²
(Measurement 1: Summary of Stability of Emulsion/Dispersion Solution of Triolein)

The table below shows the results for observation of stability of each of the triolein emulsified solutions produced in Comparative Example 2 and Examples 1-1, 1-2, and 1-3.

TABLE 1

| | Mean particle size (μm) | Stability of emulsified solution | Long-term preservation properties of emulsified solution |
|---|---|---|---|
| Comparative Example 2 | 1.693 | Observed with reaggregation within 1 hour | Observed with reaggregation within 1 hour |
| Example 1-1 | 0.19 | Stabilized for 24 hours | Stabilized for 2 weeks (cold storage) |
| Example 1-2 | 0.37 | Stabilized for 6 hours | Stabilized for 2 weeks (cold storage) |
| Example 1-3 | 0.70 | Stabilized for 6 hours | Stabilized for 2 weeks (cold storage) |

When triolein was finely dispersed, the stability of the emulsified product was increased.
(Measurement 2)

Measurement Example 1

Transfer (Leakage) of Triolein from a Lipase Analytical Element (Obtained in the Step of "Addition of a Substrate")

(1) Transfer from the Fabric Surface of a Lipase Analytical Element (Obtained in the Step of "Addition of a Substrate") to the Fabric Surface of an FDC TG Slide A piece with a size of 4×3 cm was excised form the substrate-applied product obtained in each of the above Examples. The mount of a TG slide was opened and a coated product with a size of 1.2×1.3 cm was removed therefrom. Then, the fabric surface of the substrate-applied product obtained in the above Example was scratched with the TG-coated product for transfer of triolein. Then, the slide was remounted with a mount processing apparatus. Thereafter, 7% human albumin physiological saline was spotted thereon with the use of an FDC 7000 analyzer. Then, the intensity of color development corresponding to the amount of triolein transferred was measured (as reflection density "ODr" (4 min)) 4 minutes later. In addition, for a control, fabric to which no reagent had been added was also subjected to scratching of the fabric surface, followed by measurement in the same manner as above. Then, a difference of both measurement values (ΔODr) was calculated.

Measurement Example 2

Transfer (Leakage) of Triolein from a Lipase Analytical Element (Production Intermediate)

(1) Leakage of Triolein from a Fabric Developing Layer Surface

TABLE 2

| Formulation of analytical element | Substrate | Reflective optical density of TG slide (ODr (4 min)) | ΔODr (4 min) (slide-control) | Transfer rate (relative to 100% in Comparative Example) |
|---|---|---|---|---|
| Control (developing layer with no addition of reagent) | | 0.325 | 0.000 | 0% |

TABLE 2-continued

| Formulation of analytical element | Substrate | Reflective optical density of TG slide (ODr (4 min)) | ΔODr (4 min) (slide-control) | Transfer rate (relative to 100% in Comparative Example) |
|---|---|---|---|---|
| Comparative Example | | 0.798 | 0.473 | 100% |
| Example 2-1 | Example 1-1 | 0.366 | 0.041 | 8.7% |
| | Example 1-2 | 0.375 | 0.050 | 10.6% |
| | Example 1-3 | 0.390 | 0.065 | 13.7% |
| Example 2-2 | Example 1-1 | 0.365 | 0.040 | 8.5% |
| | Example 1-2 | 0.376 | 0.051 | 10.8% |
| | Example 1-3 | 0.391 | 0.066 | 13.9% |
| Example 3-1 | Example 1-1 | 0.350 | 0.025 | 5.3% |
| | Example 1-2 | 0.355 | 0.030 | 7.4% |
| | Example 1-3 | 0.368 | 0.043 | 9.1% |
| Example 3-2 | Example 1-1 | 0.348 | 0.023 | 4.9% |
| | Example 1-2 | 0.354 | 0.029 | 6.1% |
| | Example 1-3 | 0.370 | 0.045 | 9.5% |

Compared with the Comparative Example, the amount of triolein transferred was significantly suppressed in Examples 2-1 and 2-2. In addition, further improved suppression effects were confirmed in Examples 3-1 and 3-2. Also, it was confirmed that as the particle size of the emulsion becomes smaller, the amount of triolein transferred becomes smaller.

Based on the above table, it is understood that the amount of triolein transferred becomes smaller with the use of the method in which triolein was added as an emulsified dispersion than with the use of the method in which triolein was dissolved in ethanol so as to be added. Further, it is understood that the amount of triolein transferred can be decreased by adding a hydrophilic polymer.

(Measurement 3) Technical Troubles Due to Slipping Observed During Delivery in the Step of Producing a Dry Analytical Element for Lipase:

Delivery of the production intermediates to which triolein had been added, obtained in Comparative Example 1 and Examples 2-1 and 3-1, was carried out at 30 m/minute in a manner such that the support side of each intermediate was allowed to adhere to a delivery roller (made of stainless steel). The results are shown below.

TABLE 3

| | Substrate, and addition method | Slipping length at 150-m delivery |
|---|---|---|
| Comparative Example 1 | Triolein is dissolved in ethanol | 40 m |
| Example 2-1 | Example 1-1: Emulsified dispersion(water) | 13 m |
| | Example 1-2: Emulsified dispersion(water) | 13.5 m |
| | Example 1-3: Emulsified dispersion(water) | 14 m |
| Example 3-1 | Example 1-1: Emulsified dispersion(water) | 0 m |
| | Example 1-2: Emulsified dispersion(water) | 0 m |
| | Example 1-3: Emulsified dispersion(water) | 0.5 m |

In the case of the method in which triolein was added as an emulsion/dispersion solution (Example 1), slipping length was decreased, as compared with the method in which triolein was dissolved in ethanol and was added (Comparative Example 1). Further, in the case of the method in which a hydrophilic polymer was added to a triolein emulsion/dispersion solution, it is understood that no slipping occurred. Further, it was confirmed that as the average particle size of the emulsion product becomes smaller, then slipping was less likely to occur.

The invention claimed is:

1. A method for producing a dry analytical element for measurement of pancreatic lipase contained in a body fluid which contains triglyceride of long chain alkyl fatty acid having 12 to 22 carbon atoms, monoglyceride lipase, and a glycerine measurement reagent, and comprises a water-impermeable support and at least one spreading or reagent layer, said method comprising the step of coating an emulsion/dispersion solution of triglyceride with an average particle size of 1 μm or less.

2. The method according to claim 1, wherein the average particle size of triglyceride is 0.5 μm or less.

3. The method according to claim 1, wherein the average particle size of triglyceride is 0.3 μm or less.

4. The method according to claim 1, wherein the emulsion/dispersion solution of triglyceride is prepared by high-pressure emulsification at a pressure of 100 MPa or more.

5. The method according to claim 1, wherein the emulsion/dispersion solution of triglyceride contains a hydrophilic polymer.

6. The method according to claim 1, wherein the emulsion/dispersion solution of triglyceride contains a hydrophilic polymer at 5 g/m$^2$ or more.

7. The method according to claim 1, wherein the emulsion/dispersion solution of triglyceride contains a hydrophilic polymer at 10 g/m$^2$ or more.

8. The method according to claim 5, wherein the hydrophilic polymer is a hydrophilic polymer selected from the group consisting of polyvinyl pyrrolidone, polyacrylamide, a cellulose derivative, gelatin, and combination thereof.

9. The method according to claim 8, wherein the cellulose derivative is hydroxypropyl cellulose, hydroxyethyl cellulose, or methyl cellulose.

10. The method according to claim 5, wherein the emulsion/dispersion solution of triglyceride contains at least hydroxypropyl cellulose or gelatin.

11. The method according to claim 1, wherein triglyceride is triolein.

12. The method according to claim 1, wherein monoglyceride lipase is derived from *Bacillus stearothermophilus* H-165.

13. The method according to claim 1, wherein the glycerine measurement reagent contains glycerokinase, glycerophosphate oxidase, peroxidase, and a coloring reagent.

14. The method according to claim 1, wherein the dry analytical element for measurement of pancreatic lipase contained in a body fluid comprises a water-impermeable support, a reagent layer, and a spreading layer.

15. The method according to claim 1, wherein the spreading layer comprises a fabric or a porous membrane.

16. The method according to claim 15, wherein the porous membrane is a porous membrane of polysulfone or acetyl cellulose or a porous membrane formed with fine beads.

17. A dry analytical element for measurement of pancreatic lipase contained in a body fluid, which is produced by the method according to any one of claims 1 to 16.

* * * * *